United States Patent [19]

Salamon et al.

[11] Patent Number: 5,175,297
[45] Date of Patent: Dec. 29, 1992

[54] METHYL-QUINOLINE DERIVATIVES AS MEFLOQUIN INTERMEDIATES AND PROCESS FOR PREPARATION THEREOF

[75] Inventors: Zoltán Salamon, Debrecen; József Jekő; Ilona Imre, both of Tiszavasvári; Magdolna Czellér, Hajdunánás, all of Hungary

[73] Assignee: Alkaloida Vegyeszeti Gyar, Tiszavasvari, Hungary

[21] Appl. No.: 671,917

[22] PCT Filed: Jul. 20, 1990

[86] PCT No.: PCT/HU90/00049
§ 371 Date: Mar. 19, 1991
§ 102(e) Date: Mar. 19, 1991

[87] PCT Pub. No.: WO91/01314
PCT Pub. Date: Feb. 7, 1991

[30] Foreign Application Priority Data

Jul. 25, 1989 [HU] Hungary ............................ 3736/89

[51] Int. Cl.⁵ ............................................ C07D 403/06
[52] U.S. Cl. ...................................... 546/176; 546/174
[58] Field of Search ................................ 546/174, 176

[56] References Cited

FOREIGN PATENT DOCUMENTS

WO91/01314  2/1991  PCT Int'l Appl. .

Primary Examiner—David B. Springer
Attorney, Agent, or Firm—Herbert Dubno; Jonathan Myers

[57] ABSTRACT

The present invention relates to a process for the preparation of methyl-quinoline derivatives, useful as meflocin intermediates, of the formula (I)

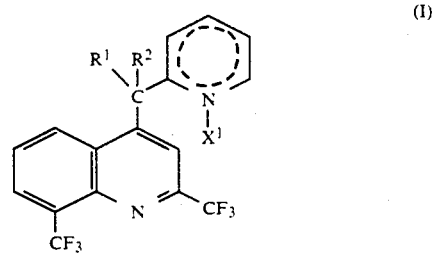

or salts thereof, wherein
$X^1$ stands for hydrogen or a non-binding electron pair,
$R^1$ stands for hydrogen or a group of the formula (II)

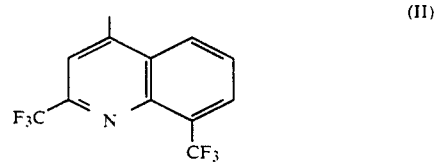

$R^2$ stands for acyloxy or hydroxyl and the dotted line indicates an optionally aromatic ring.

10 Claims, No Drawings

METHYL-QUINOLINE DERIVATIVES AS MEFLOQUIN INTERMEDIATES AND PROCESS FOR PREPARATION THEREOF

FIELD OF THE INVENTION

The present invention relates to a process for the preparation of methyl-quinoline derivatives of the formula (I)

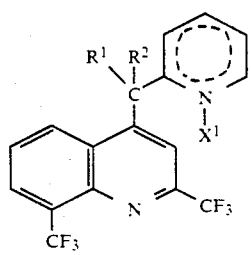

and salts thereof. The compounds of the formula (I) can be prepared by rearranging an N-oxide derivative of the formula (III)

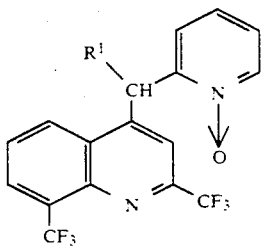

with an organic carboxylic acid derivative containing halogen, preferably with a halogene substituted $C_{1-8}$ aliphatic or aromatic carboxylic anhydride or carboxylic acid halide and by reducing the obtained ester of the formula (IV)

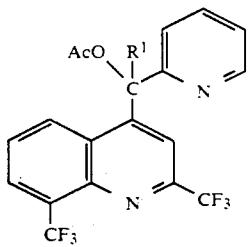

after or before solvolizing the ester group. The definition of the substituents in the present application is as follows:
$X^1$ stands for hydrogen or a non-binding electron pair,
$R^1$ stands for hydrogen or a group of the formula (II)

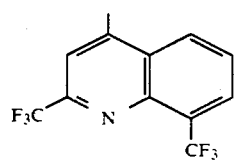

$R^2$ stands for acyloxy or hydroxyl,
$R^3$ stands for a group of the formula (II) and
Ac stands for an acyl group and
the dotted line indicates an optionally aromatic ring.

The compounds prepared according to the present invention are novel important intermediates for the preparation of pharmaceutically active compounds. Thus erythro-alfa-2-piperidyl-2,8-bis(trifluoro-methyl)-quinoline-4-methanol-hydrochloride (meflocin) can be prepared from the above compounds. This active ingredient can be used as antimalaria substance.

BACKGROUND OF THE INVENTION

Meflocin has been first prepared (J. Med. Chem. 14 926 (1971)) by hydrating 2-pyridyl-2,8-bis(trifluoro-methyl)-quinolyl-ketone ("Ketone" hereinafter) above Adams catalyst and 2-pyridyl-2,8-bis(trifluor-methyl)-quinolyl-ketone is obtained from 2,8-bis(trifluoro-methyl)-quinoline-4-carboxylic acid synthetized in three steps with 2-lithio-pyridine. Starting from the above quinoline carboxylic acid intermediate "ketone" has been obtained also by reacting same with 2-bromo-magnesium-pyridine (DOS 29 40443) which analogously was hydrogenated to mefloquin in the presence of platina-charcoal catalyst. (2-pyridyl)-2,8-bis(trifluoro-methyl)-quinoline-4-methanol which is an unisolated intermediate of the reduction step is called hereinafter "Oxy-methane". This Oxy-methane can be also obtained by subjecting 2,8-bis(trifluoro-methyl)-4-bromo-quinoline to lithiation and by reacting the formed 4-lithio-quinoline derivative with 2-pyridine-aldehyde (DOS 28066909). According to a recent approach the metallation step is eliminated so that the use of less expensive starting material than quinoline intermediates became possible. By reacting 2,8-bis(trifluoro-methyl)-4-chloro-quinoline with 2-pyridyl-aceto-nitrile or 2-pyridyl-methyl-phosphoniumsalt "ketone" is obtained by oxidizing the formed intermediate. According to the authors for the nucleophilic substitution of the halogen of the quinoline in the four-position the pyridine derivative has to contain an electron withdrawing substituent on the methyl group (such as the above mentioned carbonitrile or phosphonium group) (EP 0049776).

The industrial realization of the above described processes has several disadvantages, such as the mentioned metallation steps and the expensive quinoline intermediates, such as 2,8-bis(trifluoro-methyl)-4-bromo-quinoline or the corresponding quinoline-4-carboxylic acid (due to the use of the expensive and not easily available pyridine derivatives as disclosed above.

DESCRIPTION OF THE INVENTION

These disadvantages are eliminated by the process of the invention, according to which quinoline intermediate of the formula (III) obtained by our method disclosed in U.S. Pat. No. 4,599,345 and U.S. Pat. No. 4,659,834 suitable for the industrial synthesis of 2,8-bis(-trifluoro-methyl)-4-chloro-quinoline and 2-methyl-pyridine-N-oxide.

In the course of our experiments we have found that as opposed to the above said teaching in EP 0 049 776 there is no need to have an electron withdrawing substituent on the methyl group of picoline and a less expensive and more readily available 2-methyl-pyridine-N-oxide can be reacted without this substituent. The preparation of the N-oxide compounds is described in our Hungarian patent application No. .3736/89, 3736/89 (corresponding to PCT/HU90100080 and U.S. application Ser. No. 671,916 whereas according to the present invention the oxymethane derivative is obtained by rearranging the above compounds.

According to the present invention an N oxide of the formula (III) is reacted with trifluoro-acetic acid anhydride.

One may also proceed by reacting an N-oxide of the formula (III) with an optionally halogen substituted $C_{1-8}$ saturated or unsaturated alkanoyl halide or aroyl or heteroaroyl halide. The use of acid chlorides is preferred. The reaction is preferably carried out without solvents or in an aprotic polar or aprotic apolar organic solvent, preferably in trichloroethane, in dichloroethane or toluene. The intermediate ester is solvolyzed in an aqueous or anhydrous $C_{1-4}$ alcohol in the presence of alkali metal hydroxide, ammonia or amines, or alkali alcoholates or carbonates, preferably with sodium methylate in methanol.

One may also proceed by performing the solvolysis of the intermediate ester in alcohols by using inorganic acid catalysis, preferably in aqueous hydrochloric acid in ethanol.

In the course of the process a product of appropriate purity is obtained, if in the reaction only the compound of the formula (IV) or only the compound of the formula (V)

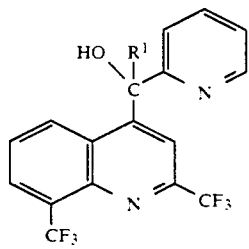

(V)

is isolated. A very pure product is obtained if N-oxide derivative of the general formula (III) is rearranged with trifluoro-acetic acid anhydride and then the compound of the general formula (V) is isolated from the reaction mixture without isolating the compound of the formula (IV) and is reduced in the presence of an alkanol.

The ester is solvolyzed in water or alcohols, or in the mixture thereof with ammonia or amines or alkoxides, preferably with sodium-methylate or triethyl-amine in methanol under mild conditions, such as room temperature or by acid catalysis in water in aqueous organic solvent, preferably in aqueous ethanol containing hydrochloric acid.

The starting N-oxides of the formula (III) can be used without isolation in situ if they were prepared according to our co-pending Hungarian patent application Nos. 3736/89, 3738/89 (corresponding to PCT/HU90100080 and U.S. application Ser. No. 671,916.

The present invention further provides novel compounds such as the compounds of the formula (III), their salts with strong inorganic acids as well as compounds of the general formulae (IV) and (VI).

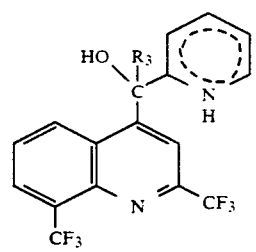

(VI)

SPECIFIC EXAMPLES

The further details of our invention are illustrated by the following examples.

EXAMPLE 1

0.78 ml of acetyl-chloride are added dropwise in 10 ml dichloro-methane to a solution of 3.70 g (N-oxy-2-pyridyl)-2,8-bis(trifluoro-methyl)-quinoline-4-methane in 50 ml of dichloro-methane at 0° C. After four days at room temperature the mixture is poured on ice, neutralized with solid potassium carbonate, the two layers are separated and the aqueous layer is extracted with $3\times40$ ml of dichloro-methane. The combined organic layer is dried above sodium sulphate and evaporated. 3.80 g of residual oil is crystallized from hexane. 2.55 g of 2-pyridyl-2,8-bis(trifluoro-methyl)-quinoline-4-methanol-acetate are obtained, and after recrystallization from isopropanol or hexane the product melts at 104°-106° C.

EXAMPLE 2

1.54 g of benzoyl-chloride are added dropwise to a solution of 3.70 g (N-oxy-2-pyridyl)-2,8-bis(trifluoromethyl)-4-quinoline-methane in 50 ml dichloro-methane at 0° C. The further proceeding is similar to that disclosed in Example 1 but the residue of the dichloro-methane extract is boiled with 230 ml of hexane and allowed to cool to room temperature and the precipitated crystalline substance is recrystallized from 1.62 g of methanol. 1.4 g of α-2-pyridyl-2,8-bis(trifluoromethyl)-quinoline-4-methanol-benzoate are obtained. Mp.: 139°-140° C.

EXAMPLE 3

20 g of (N-oxy-2-pyridyl)-2,8-bis(trifluoro-methyl)-quinoline-4-methane are mixed with 250 ml of 1,2-dichloro-ethane. Under external cooling at 25° C. 6.5 ml of ethyl-chloroformiate are added dropwise, followed by 8 ml of triethyl-amine. The mixture is allowed to stand overnight and the precipitated triethyl-amine-hydrochloride is filtered and the filtrate is evaporated at reduced pressure. The residue is recrystallized from isopropanol. 20.6 g of ethyl-(α-2-pyridyl-2,8-bis-(trifluoro-methyl)-quinoline-4-methanol)-carbonate are obtained. Yield: 86.2%, M.p.: 128°-130° C.

EXAMPLE 4

6 ml of trifluoro-acetic-acid anhydride are diluted with 40 ml of toluene and at room temperature the mixture is added dropwise to 3.72 g of (N-oxy-2-pyridyl)-2,8-bis(trifluoro-methyl)-quinoline-4-methane in 50 ml of toluene at room temperature. The mixture is allowed to stand for 1 day, poured on icy water and neutralized with solid sodium hydrogencarbonate and the two layers are separated. The organic layer is dried above sodium-sulphate, evaporated to 15 ml, cooled and the precipitated product is filtered and dried. 2.70 g of α-2-pyridyl-2,8-bis(trifluoro-methyl)-quinoline-4-methanol are obtained. M.p.: 133°–135° C.

EXAMPLE 5

20 g of (N-oxy-2-pyridyl)-2,8-bis(trifluoro-methyl)-quinoline-4-methane are dissolved at 30° C. in 25 ml of acetonitrile and 15 ml of trifluoro-acetic acid anhydride are added. After 1 hour 5 ml of water are added dropwise, the solution is evaporated at reduced temperature to 34 g and it is crystallized from isopropanol. 16.56 g of α-2-pyridyl-2,8-bis(trifluoro-methyl)-quinoline-4-methanol trifluoro-acetate salt are obtained, m.p.: 133°–135° C.

EXAMPLE 6

The reaction is carried out according to Example 5 in 250 ml of dichloro-ethane or 250 ml of dichloro-methane but 8.6 ml of trifluoro-acetic acid anhydride are used only. To the mixture 8.6 g of potassium-carbonate dissolved in 10 ml of water are added, the two layers are separated and the organic layer is clarified by charcoal, evaporated to about 1/5 and cooled.

The precipitated product is filtered and recrystallized from isopropanol. 12.63 g of α-2-pyridyl-2,8-bis(trifluoromethyl)-quinoline-4methanol are obtained, melting at 138°–140° C.

EXAMPLE 7

Ethyl-(α-2-pyridyl-2,8-bis(trifluoro-methyl)-quinoline-4-methanol)-carbonate obtained according to Example 3 is boiled in 2.2 g (30 ml) of methanol in the presence of 2.8 g of potassium-carbonate for 6 hours. The mixture is cooled to room temperature, the inorganic salt is filtered and the filtrate is acidified with glacial acetic acid (pH=6) and cooled. The precipitated product is isolated as described above. 1.4 g of α-2-pyridyl-2,8-bis(trifluoro-methyl)-quinoline-4-methanol is obtained (76%), melting point: 138°–140° C.

EXAMPLE 8

2 g of (N-oxy-2-pyridyl)-2,8-bis(trifluoro-methyl)-quinoline-4-methane are stirred for 1.5 hours at 50°–55° C. in 20 ml of propionic acid chloride. The reaction mixture is evaporated at an inert temperature of up to 70° C. at reduced pressure and the residue is poured on ice, extracted with chloroform and the evaporated residue is crystallized or recrystallized from hexane. 1.27 g of α-2-pyridyl-2,8-bis(trifluoro-methyl)-quinoline-4-methanol-propionate are obtained.

NMR data: quinoline skeleton proton shifts: 8.60 pieces, 5; 8.13 pieces, 7; 8.00 s, 3; 7.72 dd, 6; pyridine-proton shifts: 8.55 d$^3$, 6; 7.65 d$^3$, 4; 7.55 dm, 3; 7.24 d$^3$, 5; Other: 7.65 s, methine; 2.60 q, methylene; 1.22 t methyl.

EXAMPLE 9

One may proceed as given in Example 8 but 20 ml of butyric acid chloride are used. 1.72 g of α-2-pyridyl-2,8-bis(trifluoro-methyl)-quinoline-4-methanol-butyrate are obtained, m.p.: 68°–71° C.

EXAMPLE 10

10 g of di(2,8-bis(trifluoro-methyl)-4-quinolyl)-(N-oxi-2-pyridyl)-methane are dissolved in 90 ml of acetic acid anhydride and the mixture is stirred for 2 hours at 60° C. It is evaporated at reduced pressure, the residue is poured on ice and neutralized with potassium carbonate and extracted with chloroform. The organic layer is dried, evaporated and the residue is crystallized from a mixture of chloroform and hexane. Yield: 6.3 g (79.1%). The obtained α,α-di(2,8-bis(trifluoro-methyl)-4-quinolyl)-pyridine-2-methanol-acetate melts at 228°–230° C.

EXAMPLE 11

1 g of α,α-di(2,8-bis(trifluoro-methyl)-4-quinolyl)-pyridine-2-methanol-acetate is dissolved in 10 ml of anhydrous methanol and to the solution 0.1 ml of 5 mole methanolic sodium methylate is added at room temperature under nitrogen streem. The mixture is allowed to stand overnight and is neutralized with glacial acetic acid, evaporated in vacuo and the residue is crystallized from a mixture of hexane and chloroform by hot clarification. The obtained product is filtered and 0.74 g of α,α-di(2,8-bis(trifluoro-methyl)-4-quinolyl)-pyridine-2-methanol is obtained. Yield: 78.9%.

M.p.: 200°–202° C.

EXAMPLE 12

1.4 g of α-2-pyridyl-2,8-bis(trifluoro-methyl)-quinoline-4-methanol-acetate is boiled under reflux for 3 hours in 20 ml of 95% ethanol in the presence of 20 ml of 36% hydrochloric acid. The mixture is clarified hot with active charcoal, cooled and added to a suspension of 0.9 g 10% Pt/C catalyst (Aldrich) prehydrated in 80 ml of 95% ethanol. The mixture is stirred vigorously in a hydrogen atmosphere under normal pressure for 6 hours (hydrogen consumption 240 ml). The catalyst is filtered, evaporated at reduced pressure and the 1.24 g residue is recrystallized from acetonitrile. 0.96 g of erythro-α-(2-piperidyl)-2,8-bis(trifluoro-methyl)-quinoline-4-methanol-hydrochloride is obtained.

M.p.: 263°–264° C.

EXAMPLE 13

1.0 g of α-2-pyridyl-2,8-bis(triflouro-methyl)-quinoline-4-methanol acetate is added to a suspension of 0.9 g of 5% Pt/C catalyst prehydrated in 100 ml 95% ethanol and 2 ml of 36.0% hydrochloric acid. The hydrogenation is carried out as disclosed in Example 12 and the product is isolated. After recrystallization 1.0 g of erythro-α-2-piperidyl-2,8-bis(triflouro-methyl-quinoline-4-methanol-acetate hydrochloride is obtained. Yield: 90.7%. M.p.: 211°–212° C.

EXAMPLE 14

1.0 g of erythro-α-2-piperidyl-2,8-bis(triflouro-methyl)-quinoline-4-methanol-acetate hydrochloride is dissolved in 5 ml if 95% ethanol, 1.00 ml of concentrated hydrochloric acid is added and the mixture is boiled under reflux for 2 hours. It is evaporated to dryness at reduced pressure, triturated with minimal amount of acetonitrile and 0.86 g, 94.7% of erythro-α-2-piperidyl-2,6-bis(triflouro-methyl)-quinoline-4-methanol-hydrochloride is obtained.

M.p.: 259°–261° C.

We claim:

1. Process for the preparation of methyl-quinoline-derivatives of the formula (I)

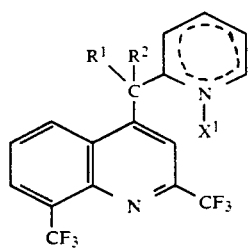

or acid addition salts thereof, wherein
$X^1$ stands for hydrogen or a non-binding electron pair,
$R^1$ stands for hydrogen or a group of the formula (II)

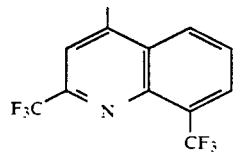

$R^2$ stands for carboalkoxyoxy, aliphatic or aromatic carboxylic acyloxy or hydroxyl
and the dotted line indicates an optionally aromatic ring, which comprises acylating and rearranging an N-oxide derivative of the formula (III)

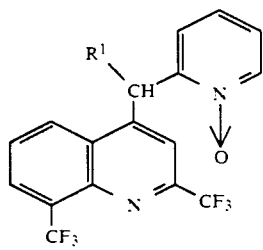

with an unsubstituted or halogen substituted aliphatic or aromatic carboxylic acid anhydride or carboxylic acid halide containing 1 to 8 carbon atoms or with a haloformic acid alkyl ester, and reducing the obtained ester of the formula (IV)

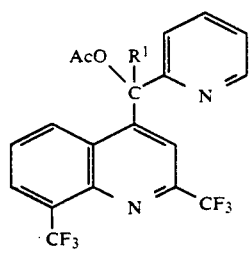

wherein Ac stands for carboalkoxy or aliphatic or aromatic carboxylic acyl-after or before the solvolysis of the ester group.

2. A process as claimed in claim 1 which comprises rearranging an N-oxide of the formula (III) with trifluoro-acetic-acid anhydride.

3. A process as claimed in claim 1 which comprises reacting an N-oxide of the formula (III) wherein $R^1$ is as given above-with a halogen substituted $C_{1-8}$ saturated or unsaturated alkanoyl halide or aroyl halide.

4. A process as claimed in claim 2 which comprises reacting the components without solvent or in an aprotic polar or aprotic apolar organic solvent.

5. A process as claimed in claim 1 which comprises performing the solvolysis of the compound of the formula (IV) in aqueous or anhydrous $C_{1-4}$ alcohols in the presence of an alkali metal hydroxide, ammonia or amine or alkali alcoholates or carbonates.

6. A process as claimed in claim 1 which comprises performing the solvolysis of the compound of the formula (IV) in alcohols and by inorganic acid catalysis.

7. A process as claimed in claim 1 which comprises isolating in the course of the reaction only compounds of the formula (IV) or only compounds of the formula (V)

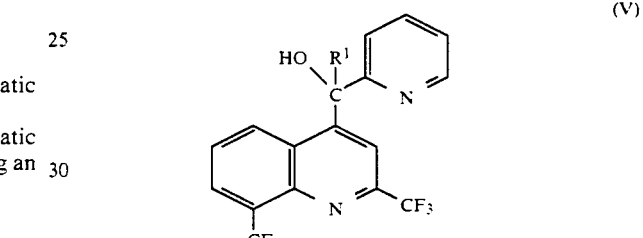

8. A process as claimed in claim 1 which comprises rearranging an N-oxide derivative of the formula (III), with trifluoro-acetic acid anhydride and isolating from the reaction mixture a compound of the formula (V).

9. A compound of the formula (IV),

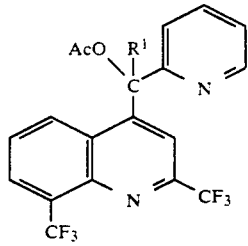

wherein $R^1$ stands for hydrogen or a group of the formula (II)

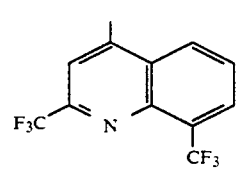

Ac stands for carboalkoxy or aliphatic or aromatic carboxylic acyl, except acetyl if $R^1$=hydrogen.

10. A compound of the Formula (VI)

(VI) 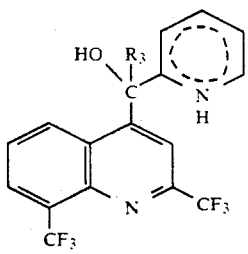
wherein R³ is a group of the Formula (II)
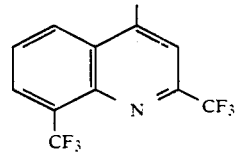
and the dotted line indicates an optionally aromatic ring.
* * * * *